United States Patent [19]
Johnson et al.

[11] Patent Number: 5,955,368
[45] Date of Patent: Sep. 21, 1999

[54] EXPRESSION SYSTEM FOR CLOSTRIDIUM SPECIES

[75] Inventors: Eric A. Johnson; Marite Bradshaw, both of Madison, Wis.; Julian I. Rood, Bentleigh; Dena Lyras, Heidelberg Heights, both of Australia

[73] Assignee: Wisconsin Alumni Research Foundation, Madison, Wis.

[21] Appl. No.: 09/056,075

[22] Filed: Apr. 6, 1998

[51] Int. Cl.[6] .............................. C12N 1/21; C12N 15/70; C12N 15/74; C12N 15/64
[52] U.S. Cl. ...................... 435/488; 435/320.1; 435/476; 435/252.3; 536/23.1; 536/24.1
[58] Field of Search .............................. 435/320.1, 172.3, 435/488, 476, 252.3; 536/23.1, 24.1

[56] References Cited

PUBLICATIONS

T.L. Bannam and J.I. Rood, "Clostridium perfringens—Escherichia coli Shuttle Vectors that Carry Single Antibiotic Resistance Determinants," Plasmid 229:223–235, 1993.

J.E. Brown and E.D. Williamson, "Molecular Approaches to Novel Vaccines for the Control of Clostridial Toxemias and Infections," The Clostridia: Molecular Biology and Pathogenesis, Academic Press, pp. 505–525, 1997.

B. Dupuy and A.L. Sonenshein, "Transcriptional Regulation of Clostridium difficile TOXA and TOXB Genes," p. 58, 1997 (Abstract).

E.A. Johnson and M. Bradshaw, "Genetic Characterization of Neurotoxin Complexes in Clostridium botulinum Type A," p. 39, 1997 (Abstract).

E.A. Johnson, et al., "Characterization of Neurotoxin Mutants in Clostridium botulinum Type A," Clin. Infect. Dis. 25(Suppl 2):S168–S170, 1997.

W.–J. Lin, "Characterization of Toxin—Negative Mutants of Clostridium botulinum 62A Produced by Transposon TN916 Mutagenesis," The Development of Genetic Methods to Study Group I Clostridium botulinum pp. 100–128, 1992.

W.–J. Lin and E.A. Johnson, "Genome Analysis of Clostridium botulinum Type A by Pulsed–Field gel Electrophoresis," App. Env. Micro. 61(12):4441–4447, 1995.

D. Lyras and J.I. Rood, "Conjugative Transfer of PR4–oriT Shuttle Vectors from Escherichia coli to Clostridium perfringens," Plasmid 39:160–164, 1998.

D. Lyras, et al., "Conjugative Transfer of Shuttle and Suicide Vectors From Escherichia coli to Clostridium perfringens," Second International Meeting on the Molecular Genetics and Pathogenesis of the Clostridia, pp. 10, 11 and 73, Jun. 22–Jun. 25, 1997 (Poster).

J. C. Marvaud, et al., "orf21 is a Positive Regulatory of Btulinum Neurotoxin and Associated Non–Toxic Protein Genes in C. botulinum,"p. 59, 1997 (Abstract).

N.P. Minton, "Molecular Genetics of Clostridial Neurotoxins," Department of Molecular Biology, Porton Down, Salisbury, UK, pp. 161–194, 19_.

E.J. Schantz and E.A. Johnson, "Properties and Use of Botulinum Toxin and Other Microbial Neurotoxins in Medicine," Micro. Rev. 56(1):80–99, 1992.

J.A. Schmidt, et al., "Development of a Reporter System to Study Neurotoxin Gene Expression in Clostridium botulinum Type A Strains," 1998.

J. Sloan, et al., "Construction of a Sequenced Clostridium perfringens–Escherichia coli Shuttle Plasmid," Plasmid 27:207–219, 1992.

T.C. Umland, et al., "The Crystal Structure of Tetanus Neurotoxin $H_C$ Fragment," p. 38, 1997 (Abstract).

Primary Examiner—Johnny F. Railey, II
Attorney, Agent, or Firm—Quarles & Brady LLP

[57] ABSTRACT

A system is used to express clostridial gene constructions in a clostridial host. A mobilizable transfer plasmid is described which permits the direct transfer of the plasmid, and genes carried on it, from E. coli into Clostridium species. A promoter is described for use in clostridial species. Also, a useful host strain is used which is nontoxigenic and which permits high levels of expression of clostridial genes using the clostridial promoter.

15 Claims, 2 Drawing Sheets

EXPRESSION SYSTEM FOR CLOSTRIDIUM SPECIES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Bacteria of the genus Clostridium are gram positive and include many pathogenic species responsible for significant mortality and morbidity in both humans and animals. The genus Clostridium produces more protein toxins than any other bacterial genus. *Clostridium tetani* is a common soil dwelling organism which produces a neurotoxin responsible for the disease tetanus. *Clostridium perfringens* is a common etiological agent of gas gangrene and food poisoning. *Clostridium difficile* is a common cause of gastroenteritis and pseudomembraneous colitis, particularly among elderly hospital patients who have had their intestinal flora depopulated by treatment with antibiotics. *Clostridium botulinum* is a heterologous collection of clostridial strains that have the common property of producing a distinctive neurotoxin (BoNT) of extraordinary potency. This neurotoxin, also known as botulinum toxin, is the cause of the severe neuroparalytic illness in humans and animals referred to as botulism. Even in advanced societies, there are fatalities each year due to oral ingestion of the botulinum toxin produced by bacteria in contaminated food sources.

Because of their extreme toxicity the neurotoxins produced by *Clostridium botulinum* have been the subject of extensive study. Botulinum toxins are classified into seven serotypes, referred to as serotypes A through G, on the basis of their immunological properties. Botulinum Type A neurotoxin is among the most poisonous natural substances known to science. The amino acid sequences of the toxins have been deduced and compared. See, for example, Minton, "Molecular Genetics of Clostridial Neurotoxins," in *Clostridial Neurotoxins*, C. Montecucco (Ed.) Springer-Verlag, Berlin (1995).

Botulinum toxin type A has become an extremely important pharmaceutical for the treatment of segmental movement disorders, spasticity, pain syndromes, and various other neuronal disorders. Botulinum toxin specifically and tightly binds to cholinergic neurons. Upon endocytosis and internalization into the nerve terminal, the light chain of the toxin acts to block or slow the exocytotic release of neurotransmitters, particularly acetylcholine. Selective injection of botulinum toxin into neuromuscular regions produces a local weakening of proximal muscles and relief from excessive involuntary muscle contractions. In addition to directly affecting cholinergic neurotransmission, botulinum toxin also exerts other poorly understood effects including altering activity of autonomic ganglia. The outstanding properties of botulinum toxin as a pharmacological agent are its specificity for peripheral nerves and its long duration of action. Complications and drawbacks of botulinum toxin therapy include immunological resistance in some patients and diffusion and resulting ptosis of neighboring muscles. These side effects can be avoided by proper expression, purification and preparation of the toxin or toxin chains or fragments for pharmaceutical use. See Schantz and Johnson, *Microbiological Reviews*, 56:80–00 (1992).

During the past decade, interest in botulinum toxins has accelerated due to the discovery that the light chains of botulinum neurotoxins specifically cleave proteins in nerve terminals that are necessary for exocytosis and neurotransmission. Interest in botulinum toxins has also been triggered by the potential for the use of these toxins in bioterrorism and, as a result, government agencies are actively investigating countermeasures against them. A pentavalent vaccine has been developed which is effective against serotypes A through E, but this vaccine is not effective against types F and G. However, the manufacturing site for this vaccine has been closed since it did not meet U.S. FDA requirements. Also, the pentavalent vaccine has drawbacks in that it can cause acute adverse reactions in some of the recipients.

Recently the U.S. Department of Defense has made an effort to produce recombinant vaccines in which fragments of botulinum toxin are produced in heterologous hosts. However, it has been found that the toxins are produced very poorly in *E. coli*, yeast, and other potential hosts. Scientists have entirely resynthesized the genes for certain serotypes to achieve better expression, but they have found that the recombinant proteins can undergo posttranslational modifications in heterologous hosts.

Botulinum toxins are found natively both in bacterial cultures and in contaminated foods complexed with other nontoxic proteins including nontoxic nonhemagglutinin (NTNH) and several hemagglutinins (HA). The neurotoxin component of the toxin complex is a 150 kDa protein comprising a heavy (HC) and a light (LC) chain. The LC contains the catalytic domain that cleaves nerve proteins essential for neurotransmission. Separation of purified toxins, or toxin domains, or toxin fragments is possible, but is difficult, laborious, and the yields are low. The clinical use of purified botulinum toxin fragments is complicated by the need for extreme care of purification, since small amounts of any contaminating active toxin can be highly dangerous. Biochemical preparations of toxin chains or fragments are always contaminated with low levels of active neurotoxin.

Two main strategies have been utilized to obtain clostridial neurotoxins, individual chains of the toxins, or non-toxigenic components of the toxin complex. The first strategy is to isolate the desired protein itself from cultures of the toxigenic *C. botulinum* strain. The second strategy is to produce the toxin or toxin fragments in heterologous hosts.

Unfortunately, the heterologous expression of clostridial genes in heterologous hosts has been found to be quite inefficient. Available information on clostridial gene expression in *E. coli* in particular, and also other heterologous hosts, indicates that the expression of clostridial genes in these hosts occurs at very low levels and is relatively inefficient. This inefficiency arises, in part, from a striking characteristic of clostridial DNA in that it has an extremely low percentage G+C content, ranging typically from 20 to 29% for toxigenic species. Oddly, the percentage G+C content of the coding regions of the clostridial genome is consistently higher than that of non-coding intergenic regions. The extremely low percentage G+C content of clostridial DNA affects the pattern of codon usage which can effect protein production in heterologous hosts which are biased toward codons in which A and T predominate. This same pattern of codon usage has been reported in many clostridial species. Because of the striking differences in codon usage, available evidence suggests that clostridial genes are inefficiently expressed in other hosts, such as *E. coli*, primarily at the translational rather than transcriptional level, although factors other than codon bias also affect expression of protein toxins. Attempts have been made to overcome this low expression problem by re-synthesizing the gene to incorporate codons preferred by E. coli or other hosts such as yeast, or to use an expression host that prefers low percentages G+C content, such as Lactococcus species. These strategies have been somewhat successfully used with the tetanus toxin.

Expression of clostridial genes in native clostridial species is, as might be expected, more efficient and the resulting proteins would be less prone to have structural or sequence errors and would undergo proper posttranslational modifications. However, prior methods for the transfer of genes into or amongst clostridial bacteria are either inefficient or non-existent. No shuttle vectors are currently available which have been shown to provide efficient gene transfer to C. botulinum. Also, handling of and culturing of these bacteria is difficult since not only are they highly toxic, the organisms are obligate anaerobes which die if exposed to oxygen. Therefore, the clostridia must be handled under specialized conditions. These technical difficulties limit the approaches that can be used for gene transfer in other bacteria such as electroporation, transformation and transduction.

Accordingly, the study and the production of clostridial toxin genes, as well as other classes of clostridial genes, would be greatly facilitated by a system that permits the introduction and expression of clostridial genes in a host of that genus which does not otherwise produce, at least prior to transformation, a toxin or toxin protein.

BRIEF SUMMARY OF THE INVENTION

The present invention is summarized in that an expression system has been developed for the expression of clostridial genes in a toxin deficient clostridial strain which makes use of a broad range host plasmid which is capable of promoting conjugative transfer of genes from E. coli to clostridial species.

It is an attribute of the clostridial gene expression system of the present invention in that it has been found that the promoter region of the nontoxic nonhemagglutinin (NTNH) gene is a particularly efficient gene expression driver in clostridial species, and, in particular, functions as an highly effective gene expression driver in strains which are toxin deficient.

The present invention is further novel in that the combination of a host strain, the shuttle plasmid, and the particular promoter, enables the high expression of any clostridial gene toxins or toxin fragments in clostridial species thereby taking advantageous use of the inherently preferential pattern of gene expression of these species for genes of species in the same genus.

Other objects, advantages, and features of the present invention will become apparent from the following specification when taken in conjunction with the accompanying drawings.

DETAILED DESCRIPTION OF THE INVENTION

Described herein are a series of components which, when taken together, make up a system which permits the efficient delivery of heterologous genes into a clostridial host, such as C. botulinum, and the expression of genes in that host. One element of this system includes a strain of C. botulinum which does not produce a toxin prior to transformation or conjugation, and therefore does not make interfering or contaminating toxin fragments or toxins which might hinder the purification or processing of heterologous toxins made in the C. botulinum strain. Also described is a clostridial promoter system which is capable of expressing genes in clostridial species and which turns out to be highly efficiently expressed in the toxin deficient C. botulinum strain used in the examples described below. Also disclosed is a shuttle vector plasmid which is capable of being constructed in commonly used bacteria, such as E. coli, and which may then be transferred by conjugation into clostridial species. Taken together, these components provide a system which permits the efficient construction of genes for expression in clostridial species, a system for the convenient transfer of genes into clostridial species, and the mechanism to ensure abundant expression of those genes once inserted into a clostridial host. Thus it becomes possible to make any number of clostridial toxins, toxin fragments, or antigenic portions thereof, in a clostridial host in a way both that ensures abundant expression and facilitates purification. Furthermore, toxins with altered structures, chimeric toxins, and other toxin derivatives valuable in medicine could be synthesized in this system.

Figure 1A:
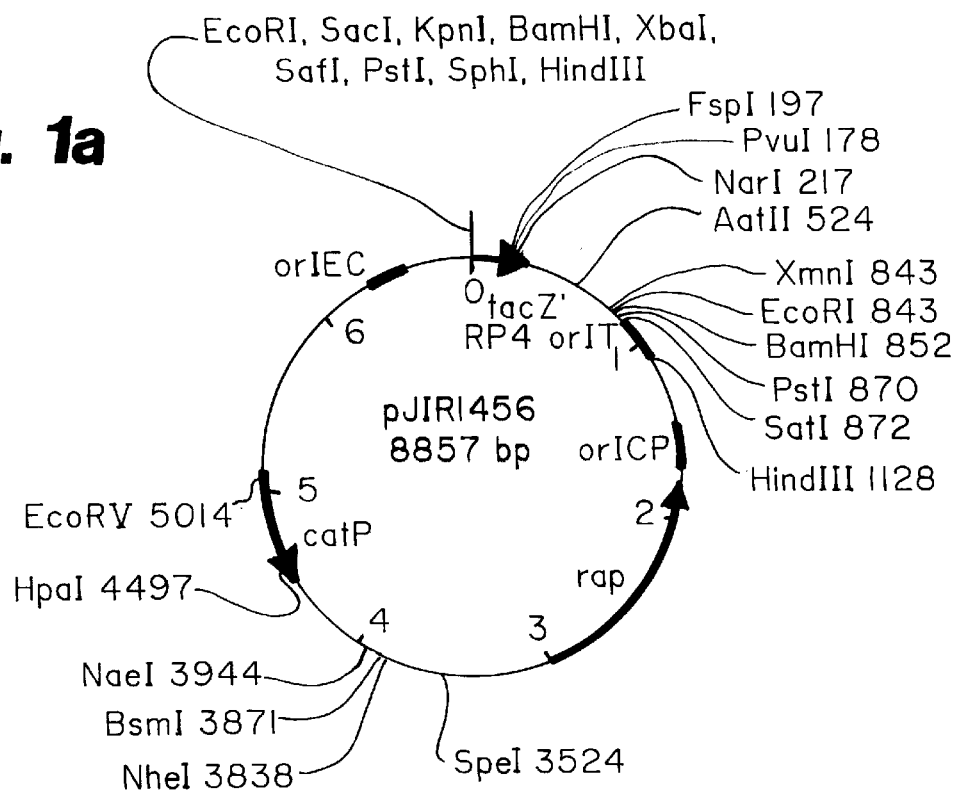
FIG. 1 is a schematic illustration of the plasmids pJIR1457 and pJIR1456.
Figure 1B:
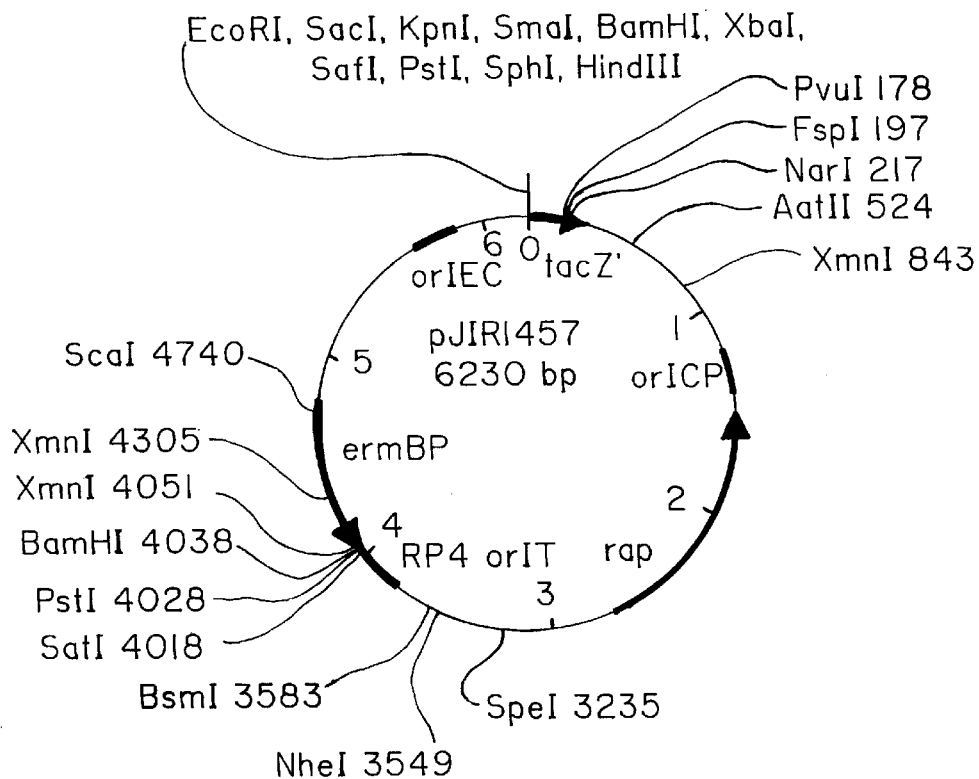

One useful component for the system of the present invention is a wide host range shuttle vector capable of transferring DNA constructs from E. coli to clostridial species in general, and to C. botulinum in particular. Illustrated at FIG. 1 is a plasmid, designated pJIR1457, described further in the examples below. This plasmid has several components common to expression vectors in bacterial hosts, and a few components which are particularly related to the unique attributes of this mobilizable transfer plasmid.

An important element of this plasmid is an origin of transfer, oriT, which comes from plasmid RP4, otherwise known as R18, R68, RK2, or RP1. RP4 is a conjugative plasmid of the incompatibility group P first found in clinical Pseudomonas aeruginosa. RP4-like plasmids have been found to have an extremely broad host range and may be involved in the dissemination of resistance genes among bacteria because they can mobilize non-conjugative plasmids which would otherwise be essentially non-transmissible. The mobilization function of the plasmid RP4 is caused by the presence of an origin of conjugative transfer, oriT, on the mobilizable plasmid. The other elements required for mobilization of the plasmid do not need to be on the plasmid, although they may be. On the illustration of the plasmid pJIR1457, the origin of conjugative transfer derived from the plasmid RP4 is indicated by the designation "RP4 oriT". It is this origin of conjugative transfer that facilitates the transfer of shuttle plasmids from E. coli into clostridial species. It has been found that this vector is capable of conjugative transfer not only to a number of C. perfringens strains, but also capable of transfer directly from E. coli into C. botulinum.

Also contained in the vector pJIR1457 is a gene encoding erythromycin resistance (ermBP) which functions in both E. coli and clostridial hosts. The designation "oriEC" indicates an origin of replication effective in E. coli, to ensure replication competency of the plasmid when in an E. coli host. The designation "oriCP" is an origin of replication intended to be effective in Clostridium perfringens. The designation "rep" refers to the essential plasmid replication gene, from Clostridium perfringens, which acts with the oriCP origin to initiate replication in clostridial hosts carrying the plasmid.

The plasmid also includes a lacZ' gene into which has been inserted a multiple cloning site, so that heterologous genes can be spliced in and colonies containing an insert detectable by the blue/white assay commonly used in bacterial expression transformation procedures.

Using the plasmid pJIR1457, or a similar plasmid (like plasmid pJIR1456 also shown in FIG. 1)which has a similar competency in both E. coli and C. botulinum, it is possible to construct recombinant plasmids intended for C. botulinum in E. coli. Competent E. coli strains harboring multiple copies of the mobilizable transfer plasmid can then be cultured in close proximity to clostridial species, such as Clostridium botulinum, under conditions favorable for conjugative transfer. Conjugative transfer will occur under those conditions and copies of the shuttle plasmid will be transferred to the clostridial species. Colonies of the clostridial species harboring this plasmid can then be isolated by antibiotic selection with erythromycin, or whichever alternative selectable antibiotic resistant selectable marker is used on the particular construct. For example, the plasmid pJIR1456 carries a chloramphenicol resistance gene.

Figure 2:
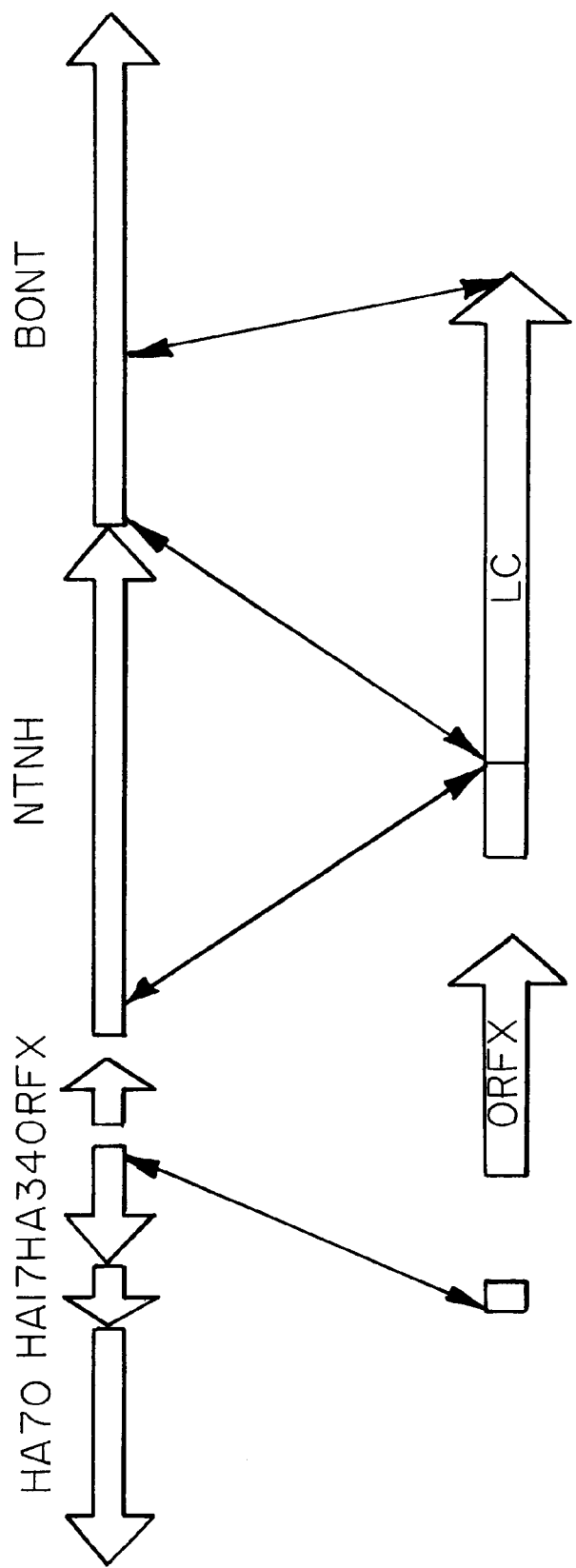
FIG. 2 is a schematic illustration of the location of the expression elements used in the practice of the invention in the examples described below.

Obviously, to prepare a genetic construct for use in Clostridium species, it is necessary to use a promoter effective in these species. Illustrated in FIG. 2 is the origin of the promoter elements used in the practice of the invention described below. On the top panel of the figure is illustrated the arrangement of gene components in the native botulinum toxin gene cluster. Open reading frames are indicated as arrows showing the orientation of transcription. The designation BoNT refers to the botulinum neurotoxin gene, while the designation NTNH refers to the nontoxic non-hemagglutinin gene and HA refers to the hemagglutinin genes. The designation ORFX refers to open reading frame X. The lower panel of FIG. 2 illustrates the components from the C. botulinum genome that were used to construct the hybrid NTNH-LC gene. This gene contains the ORFX region combined with a promoter and an amino terminal encoding region from the NTNH gene driving the expression of the light chain portion of the BONT toxin, designated in FIG. 2 as "LC". It is demonstrated in the examples described below that the promoter from NTNH is contained within this fragment and is capable of driving downstream fragments to express in C. botulinum. It is believed, but not demonstrated, that the amino terminus of the NTNH protein coding region assists in the efficient expression of the chimeric hybrid protein molecule in this host.

The availability of a C. botulinum promoter, such as that described above, makes it possible to construct artificial gene constructs in E. coli, or ex vivo, using techniques commonly known in the art today. Once such a construct is made, it can be inserted into the multiple cloning site in the mobilizable transfer vector, such as pJIR1457. The resultant plasmid can then be transferred directly from E. coli into Clostridium botulinum by conjugative transfer, where the gene will be expressed and the cells will produce protein.

In producing a protein in Clostridium botulinum, it is preferred that the C. botulinum strain does not produce other toxins, both for safety reasons and to assist in purification of whatever toxin or toxin fragment it is desired to be expressed in the host. It is for that reason that the inventors here have isolated a mutant strain of Clostridium botulinum type A. The mutant strain is a transposon mutant referred to here as LNT01. This particular strain has lost the entire neurotoxin gene cluster, in excess of 12 kb, by transposon insertion. The transposon used was Tn916, and the result was complete deletion of toxin producing activity. This strain is described in more detail by Lin and Johnson in Applied and Environmental Microbiology, 61:4441–4447 (1995) and Johnson et al, in Clinical Infectious Diseases, 25(Suppl. 2) S168–170 (1997) which are herein incorporated by reference. This strain has been deposited with the American Type Tissue Collection, 10801 University Blvd, Manassas, Va. 20110, as Accession No. 202100, under the terms of the Budapest Treaty.

The use of the promoter from the NTNH genetic component from C. botulinum in this particular nontoxigenic strain of C. botulinum appears to have had an unexpected and unusual side benefit. It was found that when a genetic construct was made using the NTNH promoter, as illustrated in the lower panel of FIG. 2, and when that construct was expressed in strain LNT01, the expression was significantly higher than that which would be experienced by native C. botulinum strains making the toxin using their native genetic components. Perhaps a repressor or regulation mechanism present to control toxin expression in native C. botulinum strains is missing from strain LNT01.

Thus it may be appreciated here that the three main elements of the system described herein operate cooperatively to allow the expression of heterologous genes in C. botulinum. The mobilizable shuttle vector allows for the construction of expression plasmids in E. coli which may then be transferred to Clostridium botulinum. The availability of the NTNH promoter allows for the expression of constructs which, when transferred into C. botulinum, will be expressed therein by native mechanisms in the host. The fact that the NTNH promoter promotes abundant gene expression when expressed in LNT01 ensures that high levels of expression can be achieved. Thus the abundant expression of toxins or other genes in Clostridium botulinum is now quite practical.

EXAMPLES

Use of Conjugative Transfer Shuttle Vector

The laboratory of inventor Dr. Rood had previously constructed a shuttle vector denominated pJIR418 which include coding sequences for both erythromycin and chloramphenicol resistance and which is described in Sloan et al., Plasmid 27:207–219 (1992). Later derivatives designated pJIR750 and pJIR751, which separately encode chloramphenicol and erythromycin resistance respectively were created as described in Bannam and Rood, Plasmid 29:233–235 (1993). The work here was intended to create derivatives of pJIR750 and pJIR751 which would carry the oriT region from RP4 so that the resultant shuttle plasmids could be mobilized by an RP4 element.

In constructing the plasmids, a 289 bp RP4 oriT-containing fragment was excised from plasmid pVWD2B (Waters et al., Proc. Nat. Acad. Sci. USA, 88:1456–1460 (1991)), using the restriction enzymes EcoR1 and HindIII, after which the fragment was treated with T4 DNA polymerase to facilitate blunt end cloning. The resulting fragment was cloned into the single XmnI (Asp700) site of the plasmid pJIR750 (at nucleotide 843) and into one of the three XmnI sites of pJIR751,(at nucleotide 3762), which lies within 2 base pairs of the end of the erythromycin resistance gene ermBP. These cloning experiments resulted in the construction of plasmids now designated as pJIR1456 and pJIR1457 illustrated in FIG. 1. The disruption of the 3' end of the ermBP gene did not adversely affect the phenotype of erythromycin resistance encoded by pJIR1457.

As can be seen with reference to FIG. 1, each of the plasmids includes a resistance gene, for erythromycin or chloramphenicol, respectively. Each of the plasmids includes an origin of replication derived from *E. coli* (oriEC) as well as an origin of replication from *Clostridium perfringens* (oriCP). In addition, both plasmids contain the rep function. In addition both plasmids contain the gene for lacZ', in which is inserted a multiple cloning site. The locus of insertion of the RP4 oriT is different, depending on the plasmids, as illustrated in FIG. 1.

Nucleotide sequencing was used to confirm the presence of the RP4 oriT fragments in both pJIR1456 and pJIR1457. The complete nucleotide sequences of the parental fragments was known and published as is that of RP4. The entire nucleotide sequence of pJIR1457 was determined and is presented here as SEQ ID NO:1. The sequence is also available as GenBank Accession No. U90555. The sequence of pJIR1456 is also available as GenBank Accession No. U90554.

To assist a review of the sequence of pJIR1457, the following is a list of features of the plasmid:

| Base pair location | Feature |
| --- | --- |
| 1–57 | pVC18-derived multiple cloning site |
| 1190–1419 | *C. perfringens* replication origin |
| 1482–2702 | *C. perfringens* replication gene |
| 3770–4013 | RP4 origin of DNA transfer |
| 3761–4787 | *C. perfringens* erythromycin resistance gene |
| 5665–5885 | *E. coli* replication origin |
| 6230–6243–310 | lacZ gene |

To demonstrate that the RP4 oriT site carried by plasmid pJIR1457 was functional, mating experiments were performed using an *E. coli* donor strain and an *E. coli* recipient strain. The *E. coli* donor strain used in these and subsequent experiments was a strain designated S17-1 which has a chromosomally integrated RP4 molecule that mobilizes appropriate non-conjugative or mobilizable plasmids as efficiently as autonomous RP4 plasmids. (Simon, *Biotechnology* 1:37–45 (1983)). A variety of other hosts are known which contain RP4 elements. The advantage of using S17-1 is that the RP4 plasmid cannot be transferred to the recipient cells since it is chromosomally integrated. As was hoped, the plasmid pJIR1457 was mobilized into recipient *E. coli* strains at high frequencies. The transfer of frequency to *E. coli* strain LT101, for example, was $3.8 \pm 0.2 \times 10^{-1}$. This transfer frequency represents the number of transconjugants per donor cell and represented the average of three independent experiments. The *E. coli* to *E. coli* matings were performed using the spot mating method of Fong and Stanisich, *J. Gen. Microbiol.*, 135:499–502 (1989). The medium used was 2YT agar or broth medium supplemented with rifampicin at 150 μg/ml and erythromycin at 150 μg/ml when selecting for transconjugants carrying pJIR1457.

Subsequently similar mating experiments were performed using the S17-1 strains harboring the pJIR1457 plasmid as a donor and the *Clostridium perfringens* strain JIR325 as the recipient host. *E. coli* to *C. perfringens* matings were performed anaerobically using a plate mating method essentially as described previously in Rood et al., *Plasmid*, 1:563–570 (1978) except that logarithmic phase *E. coli* cells grown in 2YT broth were used as donors. In addition, selection of *C. perfringens* transconjugants was performed using nutrient agar supplemented with rifampicin at 20 μg/ml and nalidixic acid at 20 μg/ml together with erythromycin at 50 μg/ml. Under these conditions it was found that the transfer frequency to *C. perfringens* was at the rate of $2.2 \pm 0.4 \times 10^{-3}$.

The transfer frequencies obtained into *C. perfringens* were similar to those obtained when a control *C. perfringens* to *C. perfringens* mating was performed using the conjugative *C. perfringens* plasmid pCW3. The result indicates that matings between an *E. coli* donor and a *C. perfringens* recipient can be as efficient as those between the *C. perfringens* donor and recipient. The RP4 encoded conjugation machinery can therefore be efficiently used to transfer an artificially constructed DNA construct from *E. coli* to *C. perfringens* at reasonable frequencies.

To verify the nature of the transconjugants, the plasmid pJIR1457 was re-isolated from three independently derived *C. perfringens* transconjugants. The restriction profiles of the plasmids were identical to those of the parental plasmids indicating that a passage through *C. perfringens* did not lead to any deletions or rearrangements.

Transfer and Expression in *Clostridium botulinum*

Lacking any concrete evidence as to what genetic constructs could be transferred into *Clostridium botulinum*, it was decided to conduct an empirical experiment to see if the shuttle plasmid pJIR1457 could work in *C. botulinum* species. Again the attempt was made to transfer genetic constructs from an *E. coli* strain harboring the genetic elements necessary for the mobilization host, and again the *E. coli* strain S17-1 which carries a derivative of the broad host range RP4 plasmid was used.

Initially, *E. coli* strain S17-1 carrying the plasmid pJIR1457 was mated with three *C. botulinum* type A strains, the strains being those referred to as 62A, the 62A/Tn916 nontoxigenic strain known as LNTO1, and HallA. In these experiments, bacterial cultures were grown to late log phase and 100 μl of each culture are mixed together and spread over the surface of thick BHI agar plates and grown anaerobically at 37° C. for 36 hours. Bacterial growth was removed from the mating plates with 3 ml of nutrient broth, diluted, and plated on BHI plates containing 250 μg/ml cycloserine, 76 μg/ml sulfamethazole (selective for proteolytic *C. botulinum*), 50 μg/ml erythromycin (to select for the plasmid) and additionally 10 μg/ml tetracycline (which is selective for Tn916), the later being used only for the mating pair *E. coli* S17-1/*C. botulinum* LNTO1. The plates were incubated anaerobically at 37° C. for 36 hours. Individual colonies were re-isolated on fresh BHI plates with the same selective antibiotics and incubated anaerobically for 24 hours at 37° C. None of the three *C. botulinum* parental strains or the *E. coli* S17-1 strain harboring the pJIR1457 plasmid grew on the selective plates. Random colonies were picked and grown anaerobically for 12 hours at 37° C. in 10 ml of TPGY broth supplemented with appropriate antibiotics. Cells were harvested by centrifugation from 3 ml of the cultures and plasmid DNA was isolated. All clones contained DNA corresponding in size to pJIR1457 isolated from *E. coli* strain S17-1. The restriction enzyme digests of pJIR1457 isolated from *E. coli*, and those isolated from the *C. botulinum* transconjugants, revealed the same pattern upon restriction digestion analysis demonstrating that the plasmid was unaltered by its passage through *C. botulinum* hosts.

The transconjugants stained gram-positive and were morphologically identical to the parental *C. botulinum* strains. Botulinum neurotoxin was detected by mouse assay in culture broths from the transconjugants derived from the toxicogenic *C. botulinum* strains, but was not detected from the nontoxigenic mutant strain LNTO1. These experiments were conducted to show that the mobilizable *E. coli*/*C. perfringens* shuttle vector pJIR1457 can readily be transferred directly from *E. coli* to *C. botulinum*.

Additional studies were conducted that demonstrate that the plasmid pJIR1457 has the ability to transfer and express a cloned *C. botulinum* toxin gene. For this purpose, an artificial gene construct was manufactured that contained the coding sequence for the light chain derivative of the BONT toxin. This is the construct illustrated in FIG. 2. To prepare this hybrid, a DNA fragment was generated by PCR from *C. botulinum* strain 62A chromosomal DNA that contained a short region of the HA34 gene, ORFX, the promoter region of the NTNH gene, and the 207 base pair coding region encoding the first 69 amino acid residues of the NTNH gene. This fragment was isolated and fused in frame with a PCR fragment of the neurotoxin LC region containing 1296 base pairs encoding 432 amino acids of the BONT gene, followed by a stop codon. The complete nucleotide sequence of the hybrid gene was determined. That sequence is presented as SEQ ID NO:2 below. The hybrid gene was inserted into the plasmid pJIR1457 yielding plasmid pMB108 which was then introduced into *E. coli* strain S17-1.

In the sequence of SEQ ID NO:2, the following features can be found.

| Base pair location | Feature |
| --- | --- |
| 1–6 | EcoRI site |
| 7–77 | 5' fragment of gene HA34 |
| 304–842 | gene/ORFX |
| 855–898 | NTNH promoter |
| 1002–1208 | 5' fragment of NTNH gene |
| 1209–1214 | Bam HI site |
| 1215–2561 | The LC of botulinum toxin |
| 2565–2570 | Xba I site |

Then the plasmid pMB108 was conjugatively transferred to *C. botulinum* strains 62A and LNTO1 as described above. Plasmid DNA was isolated from randomly selected colonies of both strains, and all clones were found to contain unaltered plasmid pMB108. Selected transconjugants were tested for expression of the recombinant NTNH-LC gene. Clostridial bacterial cultures were grown anaerobically in 10 ml of TPGY broth supplemented with appropriate antibiotics at 37° C. for 96 hours. Proteins were recovered from the culture broths by precipitation with trichloroacetic acid, the proteins were separated by SDS-PAGE and transferred onto PDVF membrane. Western blots were then performed using polyclonal antibodies specific to the *C. botulinum* type A neurotoxin.

The results of this Western analysis demonstrated that the *C. botulinum* strain 62A transformed with the vector plasmid pJIR1457 produced about the same quantities of BoNT light chain as the parental strain, indicating that the presence of pJIR1457 did not affect BoNT production in this strain. This result was confirmed by a mouse assay. Toxin bands were not observed in the nontoxigenic parental strain LNTO1 or in the derivative carrying pJIR1457. However, the two transconjugants created by transfer into nontoxigenic strain LNTO1 of the hybrid gene construct pMB108 revealed bands of approximately 55 kDa, corresponding to the expected size of the hybrid gene product NTNH-LC. These same bands were also present in 62A/pMB108 transconjugants along with the native light chain, heavy chain, and the entire toxin.

One very interesting result from this experiment was that the quantity of recombinant light chain produced in the transformants of nontoxigenic bacteria was significantly higher than the quantity of recombinant light chain toxin produced in any of the wild type strains. The fact that the hybrid gene construct expresses well in the nontoxigenic bacterial strain LNTO1 suggests higher levels of expression can be achieved in at least some nontoxigenic host strains than in host strains which are still competent to produce toxic protein.

Following on from this work, it now becomes possible to use the strategy described in this example to produce high levels of clostridial proteins in a native clostridial host. This system can be used to produce clostridial proteins of many kinds and is particularly useful for production of clostridial toxins and their derivatives including toxin domains or fragments, nontoxigenic fragments, chimeric toxins and artificial toxins of modified or multiple serotype.

We claim:
1. A conjugative transfer plasmid comprising:
   an origin of replication effective in E. coli;
   an origin of replication effective in Clostridium species;
   a gene for an antibiotic resistance marker; and
   an origin of conjugative transfer which is capable of modulating the conjugative transfer of the plasmid from E. coli into a Clostridium species.
2. The conjugative transfer plasmid of claim 1 wherein the origin of conjugative transfer is RP4 oriT.
3. The conjugative transfer plasmid of claim 1 further comprising a genetic construction effective to express an antibiotic resistance in Clostridium botulinum.
4. The plasmid pJIR1457.
5. The plasmid pJIR1456.
6. A method for the delivery and expression of genetic constructs in a Clostridium species comprising the steps of:
   making a genetic construction including a promoter effective in the Clostridium species;
   inserting the genetic construction in a mobilizable transfer plasmid which includes an origin of replication effective in E. coli; an origin of replication effective in a Clostridium species; a gene for an antibiotic resistance marker; and an origin of conjugative transfer which, when actuated, is capable of directing the transfer of the plasmid from E. coli into a Clostridium species;

transforming the mobilizable plasmid into an *E. coli* strain;

culturing the *E. coli* strain carrying the plasmid with a culture of the Clostridium species under conditions which facilitate conjugative transfer of the plasmid; and selecting for bacteria of the Clostridium species which are hosting the plasmid.

7. A method as claimed in claim 6 wherein the origin of conjugative transfer is RP4 oriT and wherein the *E. coli* strain harbors the RP4 genetic elements necessary to facilitate the mechanism of conjugative transfer.

8. A method as claimed in claim 6 wherein the promoter effective in Clostridium species is the NTNH promoter from *Clostridium botulinum*.

9. A method as claimed in claim 6 wherein the Clostridium species is *Clostridium botulinum*.

10. A method as claimed in claim 6 wherein the Clostridium species is *Clostridium perfringens*.

11. A genetic construct for the expression of genes in Clostridium species comprising:

the NTNH promoter from *C. botulinum*; and a protein coding sequence encoding for a protein other than the NTNH protein.

12. The genetic construction of claim 11 wherein the promoter has the DNA sequence included in SEQ ID NO:2.

13. An expression system for the efficient expression of Clostridium genes of interest comprising:

a genetic construction including a protein coding sequence for the gene of interest operably joined to the NTNH promoter from *C. botulinum*, the genetic construction placed in a mobilizable plasmid which is capable of conjugative transfer between *E. coli* and *C. botulinum*;

the genetic construct hosted in a strain of *C. botulinum* which is modified so as to not produce a botulinum toxin prior to conjugative transfer of the genetic construction into the host.

14. An expression system as claimed in claim 13 wherein the mobilizable transfer plasmid comprises an origin of replication effective in *E. coli*; an origin of replication effective in a Clostridium species; a genetic construct for an antibiotic resistance marker; and an origin of conjugative transfer which is capable of directing the transfer of the plasmid from *E. coli* into a Clostridium species.

15. An expression system as claimed in claim 13 wherein the strain of *C. botulinum* is strain LNT01.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 6243 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: misc_feature
      (B) LOCATION: 3770..4013
      (D) OTHER INFORMATION: /note= "RP4 origin of DNA transfer
          (oriT) from plasmid RP4"

(xi) SEQUENCE DESCRIPTION: SEQ ID NO:1:

```
GAATTCGAGC TCGGTACCCG GGGATCCTCT AGAGTCGACC TGCAGGCATG CAAGCTTGGC      60

ACTGGCCGTC GTTTTACAAC GTCGTGACTG GGAAAACCCT GGCGTTACCC AACTTAATCG     120

CCTTGCAGCA CATCCCCCTT TCGCCAGCTG GCGTAATAGC GAAGAGGCCC GCACCGATCG     180
```

-continued

```
CCCTTCCCAA CAGTTGCGCA GCCTGAATGG CGAATGGCGC CTGATGCGGT ATTTTCTCCT      240

TACGCATCTG TGCGGTATTT CACACCGCAT ATGGTGCACT CTCAGTACAA TCTGCTCTGA      300

TGCCGCATAG TTAAGCCAGC CCCGACACCC GCCAACACCC GCTGACGCGC CCTGACGGGC      360

TTGTCTGCTC CCGGCATCCG CTTACAGACA AGCTGTGACC GTCTCCGGGA GCTGCATGTG      420

TCAGAGGTTT TCACCGTCAT CACCGAAACG CGCGAGACGA AAGGGCCTCG TGATACGCCT      480

ATTTTTATAG GTTAATGTCA TGATAATAAT GGTTTCTTAG ACGTCAGGTG GCACTTTTCG      540

GGGAAATGTG CGCGGAACCC CTATTTGTTT ATTTTTCTAA ATACATTCAA ATATGTATCC      600

GCTCATGAGA CAATAACCCT GATAAATGCT TCAATAATAT TGAAAAAGGA AGAGTATGAG      660

TATTCAACAT TTCCGTGTCG CCCTTATTCC CTTTTTTGCG GCATTTTGCC TTCCTGTTTT      720

TGCTCACCCA GAAACGCTGG TGAAAGTAAA AGATGCTGAA GATCAGTTGG GTGCACGAGT      780

GGGTTACATC GAACTGGATC TCAACAGCGG TAAGATCCTT GAGAGTTTTC GCCCCGAAGA      840

ACGTTTTCCA ATGATGAGCA CTTTTAAATT AAAAATGAAG TTTTAAAACT TCATTTTTAA      900

TTTAAATTAA AAATGAAGTT TTATCAAAAA AATTTCCAAT AATCCCACTC TAAGCCACAA      960

ACACGCCCTA TAAAATCCCG CTTTAATCCC ACTTTGAGAC ACATGTAATA TTACTTTACG     1020

CCCTAGTATA GTGATAATTT TTTACATTCA ATGCCACGCA AAAAAATAAA GGGGCACTAT     1080

AATAAAAGTT CCTTCGGAAC TAACTAAAGT AAAAAATTAT CTTTACAACC TCCCCAAAAA     1140

AAAGAACAGG TACAAAGTAC CCTATAATAC AAGCGTAAAA AATGAGGGT AAAAATAAAA      1200

AAATAAAAAA ATAAAAAAAT AAAAAAATAA AAAAAATAAA AAATAAAAA AATAAAAAAA     1260

TAAAAAAATA AAAAAATAAA AAAATAAAAA AATAAAAAAA TATAAAAATA AAAAAATATA     1320

AAAATAAAAA AATATAAAAA TAAAAAAATA TAAAAATAAA AAAATAAAAA AATATAAAAA     1380

TAAAAAAATA AAAAAATATA AAAATATTTT TTATTTAAAG TTTGAAAAAA ATTTTTTTAT     1440

ATTATATAAT CTTTGAAGAA AAGAATATAA AAAATGAGCC TTTATAAAAG CCCATTTTTT     1500

TTCATATACG TAATATGACG TTCTAATGTT TTTATTGGTA CTTCTAACAT TAGAGTAATT     1560

TCTTTATTTT TAAAGCCTTT TTCTTTAAGG GCTTTTATTT TTTTTCTTAA TACATTTAAT     1620

TCCTCTTTTT TTGTTGCTTT TCCTTTAGCT TTTAATTGCT CTTGATAATT TTTTTTACCT     1680

CTAATATTTT CTCTTCTCTT ATATTCCTTT TTAGAAATTA TTATTGTCAT ATATTTTGT      1740

TCTTCTTCTG TAATTTCTAA TAACTCTATA AGAGTTTCAT TCTTATACTT ATATTGCTTA     1800

TTTTTATCTA AATAACATCT TTCAGCACTT CTAGTTGCTC TTATAACTTC TCTTTCACTT     1860

AAATGTTGTC TAAACATACT ATTAAGTTCT AAAACATCAT TTAATGCCTT CTCAATGTCT     1920

TCTGTAAAGC TACAAAGATA ATATCTATAT AAAAATAATA TAAGCTCTCT GTGTCCTTTT     1980

AAATCATATT CTCTTAGTTC ACAAAGTTTT ATTATGTCTT GTATTCTTCC ATAATATAAA     2040

CTTCTTTCTC TATAAATATA ATTTATTTTG CTTGGTCTAC CCTTTTTCCT TTCATATGGT     2100

TTTAATTCAG GTAAAAATCC ATTTTGTATT TCTCTTAAGT CATAAATATA TTCGTACTCA     2160

TCTAATATAT TGACTACTGT TTTTGATTTA GAGTTTATAC TTCCTGGAAC TCTTAATATT     2220

CTGGTTGCAT CTAAGGCTTG TCTATCTGCT CCAAAGTATT TTAATTGATT ATATAAATAT     2280

TCTTGAACCG CTTTCCATAA TGGTAATGCT TTACTAGGTA CTGCATTTAT TATCCATATT     2340

AAATACATTC CTCTTCCACT ATCTATTACA TAGTTTGGTA TAGGAATACT TTGATTAAAA     2400

TAATTCTTTT CTAAGTCCAT TAATACCTGG TCTTTAGTTT TGCCAGTTTT ATAATAATCC     2460

AAGTCTATAA ACAGTGTATT TAACTCTTTT ATATTTTCTA ATCGCCTACA CGGCTTATAA     2520

AAGGTATTTA GAGTTATATA GATATTTTCA TCACTCATAT CTAAATCTTT TAATTCAGCG     2580
```

```
TATTTATAGT GCCATTGGCT ATATCCTTTT TTATCTATAA CGCTCCTGGT TATCCACCCT     2640

TTACTTCTAC TATGAATATT ATCTATATAG TTCTTTTTAT TCAGCTTTAA TGCGTTTCTC     2700

ACTTATTCAC CTCCCCTTCT GTAAAACTAA GAAAATTATA TCATATTTTC AATAATTATT     2760

AACTATTCTT AAACTCTTAA TAAAAAATAG AGTAAGTCCC CAATTGAAAC TTAATCTATT     2820

TTTTATGTTT TAATTTATTA TTTTTATTAA AATATTTTAA ACTAAATTAA ATGATTCTTT     2880

TTAATTTTTT ACTATTTCAT TCCATAATAT ATTACTATAA TTATTTACAA ATAATATTTC     2940

TTCATTTGTA ATATTTAGAT GATTTACTAA TTTTAGTTTT TATATATTAA ATAATTAATG     3000

TATAATTTAT ATAAAAAATC AAAGGAGCTT ATAAATTATG ATTATTTCCA AAGATACTAA     3060

AGATTTAATT TTTTCAATTT TAACAATACT TTTTGTAATA TTATGTTTAA ATTTAATTGT     3120

ATTTTTTTCA TATAATAAAG CCGTTGAAGT AAACCAATCC ATTTTCCTTA TGATGTTATT     3180

ATTAAATTTA AGTTTTATAA TAATATCTTT ATTATATTTA TTGTTTTTAA AAAAACTAGT     3240

GAAATTTCCG GCTTATTAA ACTTATTTTT AGGAATTTTA TTTTCATTTT CATCTTTACA      3300

GGATTTGATT ATATCTTTAA ATATGTTTTA TCAAATATTA TCTTTTTCTA AATTTATATA     3360

TATTTTTATT ATATTTATTA TTATATATAT TTTATTTTTA AGTTTCTTTC TAACAGCTAT     3420

TAAAAAGAAA CTTAAAAATA AAAACACGTA CTCTAAACCA ATAAATAAAA CTATTTTTAT     3480

TATTGCTGCC TTGATTGGAA TAGTTTTTAG TAAAATTAAT TTCAATATTC CACAATATTA     3540

TATTATAAGC TAGCTTTGCA TTGTACTTTT CAATCGCTTC ACGAATGCGG TTATCTCCGA     3600

AAGATAAAGT CTTTTCATCT TCCTTGATGA AGATAAGATT TTCTCCGTCT CCGCCGACCT     3660

CTTTAGCTCC TTGGAAGCTG TCAGTAGTAT ACCTAATAAT TTATCTACAT TCCCTTTAGT     3720

AACGTGTAAC TTTCCAAATT TACAAAAGCG ACTCATAGAA TTAGCTTATC GGCCAGCCTC     3780

GCAGAGCAGG ATTCCCGTTG AGCACCGCCA GGTGCGAATA AGGGACAGTG AAGAAGGAAC     3840

ACCCGCTCGC GGGTGGGCCT ACTTCACCTA TCCTGCCCGG CTGACGCCGT TGGATACACC     3900

AAGGAAAGTC TACACGAACC CTTTGGCAAA ATCCTGTATA TCGTGCGAAA AAGGATGGAT     3960

ATACCGAAAA AATCGCTATA ATGACCCCGA AGCAGGGTTA TGCAGCGGAA AAGATCCGTC     4020

GACCTGCAGC CAAGGACGGA TCCGGGGAAT TATTTCCTCC CGTTAAATAA TAGATAACTA     4080

TTAAAAATAG ACAATACTTG CTCATAAGTA ACGGTACTTA AATTGTTTAC TTTGGCGTGT     4140

TTCATTGCTT GATGAAACTG ATTTTTAGTA AACAGTTGAC GATATTCTCG ATTGACCCAT     4200

TTTGAAACAA AGTACGTATA TAGCTTCCAA TATTTATCTG GAACATCGT GGTATGGCGG      4260

GTAAGTTTTA TTAAGACACT GTTTACTTTT GGTTTAGGAT GAAAGCATTC CGCTGGCAGC     4320

TTAAGCAATT GCTGAATCGA GACTTGAGTG TGCAAGAGCA ACCCTAGTGT TCGGTGAATA     4380

TCCAAGGTAC GCTTGTAGAA TCCTTCTTCA ACAATCAGAT AGATGTCAGA CGCATGGCTT     4440

TCAAAAACCA CTTTTTTAAT AATTTGTGTG CTTAAATGGT AAGGAATACT CCCAACAATT     4500

TTATACCTCT GTTTGTTAGG GAATTGAAAC TGTAGAATAT CTTGGTGAAT TAAAGTGACA     4560

CGAGTATTCA GTTTTAATTT TTCTGACGAT AAGTTGAATA GATGACTGTC TAATTCAATA     4620

GACGTTACCT GTTTACTTAT TTTAGCCAGT TTCGTCGTTA AATGCCCTTT ACCTGTTCCA     4680

ATTTCGTAAA CGGTATCGGT TTCTTTTAAA TTCAATTGTT TTATTATTTG GTTGAGTACT     4740

TTTTCACTCG TTAAAAAGTT TTGAGAATAT TTTATATTTT TGTTCATGTA ATCACTCCTT     4800

CTTAATTACA AATTTTTAGC ATCTAATTTA ACTTCAATTC CTATTATACA AAATTTTAAG     4860

ATACTGCACT ATCAACACAC TCTTAAGTTT GCTTCTAAGT CTTATTTCCA TAACTTCTTT     4920

TACGTTTCCG GGTACAATTC GTAATCATGT CATAGCTGTT TCCTGTGTGA AATTCTTATC     4980
```

```
CGCTCACAAT TCCACACAAC ATACGAGCCG GAAGCATAAA GTGTAAAGCC TGGGGTGCCT        5040

AATGAGTGAG CTAACTCACA TTAATTGCGT TGCGCTCACT GCCCGCTTTC CAGTCGGGAA        5100

ACCTGTCGTG CCAGAAAACT TCATTTTTAA TTTAAAAGGA TCTAGGTGAA GATCCTTTTT        5160

GATAATCTCA TGACCAAAAT CCCTTAACGT GAGTTTTCGT TCCACTGAGC GTCAGACCCC        5220

GTAGAAAAGA TCAAAGGATC TTCTTGAGAT CCTTTTTTTC TGCGCGTAAT CTGCTGCTTG        5280

CAAACAAAAA AACCACCGCT ACCAGCGGTG GTTTGTTTGC CGGATCAAGA GCTACCAACT        5340

CTTTTTCCGA AGGTAACTGG CTTCAGCAGA GCGCAGATAC CAAATACTGT CCTTCTAGTG        5400

TAGCCGTAGT TAGGCCACCA CTTCAAGAAC TCTGTAGCAC CGCCTACATA CCTCGCTCTG        5460

CTAATCCTGT TACCAGTGGC TGCTGCCAGT GGCGATAAGT CGTGTCTTAC CGGGTTGGAC        5520

TCAAGACGAT AGTTACCGGA TAAGGCGCAG CGGTCGGGCT GAACGGGGGG TTCGTGCACA        5580

CAGCCCAGCT TGGAGCGAAC GACCTACACC GAACTGAGAT ACCTACAGCG TGAGCTATGA        5640

GAAAGCGCCA CGCTTCCCGA AGGGAGAAAG GCGGACAGGT ATCCGGTAAG CGGCAGGGTC        5700

GGAACAGGAG AGCGCACGAG GGAGCTTCCA GGGGGAAACG CCTGGTATCT TTATAGTCCT        5760

GTCGGGTTTC GCCACCTCTG ACTTGAGCGT CGATTTTTGT GATGCTCGTC AGGGGGGCGG        5820

AGCCTATGGA AAAACGCCAG CAACGCGGCC TTTTTACGGT TCCTGGCCTT TTGCTGGCCT        5880

TTTGCTCACA TGTTCTTTCC TGCGTTATCC CCTGATTCTG TGGATAACCG TATTACCGCC        5940

TTTGAGTGAG CTGATACCGC TCGCCGCAGC CGAACGACCG AGCGCAGCGA GTCAGTGAGC        6000

GAGGAAGCGG AAGAGCGCCC AATACGCAAA CCGCCTCTCC CCGCGCGTTG GCCGATTCAT        6060

TAATGCAGCT GGCACGACAG GTTTCCCGAC TGGAAAGCGG GCAGTGAGCG CAACGCAATT        6120

AATGTGAGTT AGCTCACTCA TTAGGCACCC CAGGCTTTAC ACTTTATGCT TCCGGCTCGT        6180

ATGTTGTGTG GAATTGTGAG CGGATAACAA TTTCACACAG GAAACAGCTA TGACCATGAT        6240

TAC                                                                     6243

(2) INFORMATION FOR SEQ ID NO:2:

(i) SEQUENCE CHARACTERISTICS:
        (A) LENGTH: 2570 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GAATTCGTAT CGGCCTTACA GGAGATGGTA ACAATTTTGT CATTTAATGA ATTTTGGATT          60

ACTGAATAGT GTTCCATTAT GATTCCTCCT TTATTTAAGA ATTAATCTTA CATATAACAT         120

ATAACATAAT CAAATTATTT TTTGTAAACC TAAAATTTAA ATATATCAAA TTTTTATTAG         180

TATGTTTACA TAATTGATTA TGGATATTTC GTAAAAATGG CTTATTAAAA ATTTAAAGGC         240

AATTAGTTTA TTTATAGTAT AATAAAAAAA TAATATGTAT ATTATGGAAG GGTAGTGGTA         300

AATATGAATA AATTGTTTTT ACAAATTAAA ATGTTAAAAA ATGACAATAG GGAGTTTCAA         360

GAAATTTTTA AGCATTTTGA AAAAACTATA AATATATTTA CTAGAAAATA TAATATATAT         420

GATAATTACA ATGATATTTT GTACCATTTA TGGTATACAC TTAAAAAAGT TGATTTGAGC         480

AATTTCAATA CACAAAATGA TTTAGAGAGA TATATTAGTA GGACTTTAAA AAGATATTGC         540

TTAGATATTT GCAATAAAAG AAAGATTGAT AAGAAAATAA TATATAATTC AGAAATTGTA         600

GATAAGAAAT TAAGCTTAAT AGCAAATAGT TATTCAAGTT ATTTAGAATT TGAATTTAAT         660
```

-continued

```
GATTTAATAT CCATATTACC TGATGATCAA AAGAAAATTA TATATATGAA ATTTGTTGAA      720

GATATTAAGG AGATAGATAT AGCTAAAAAA CTTAATATAA GTCGTCAATC TGTATATAAA      780

AATAAAATAA TGGCTTTAGA GAGATTAGAA CCCATATTGA AAAAATTAAT TAATATGTAG      840

TTTATATTTT TAAAAAATTT TAGGTTTACA AAAAATAGTG TGGCTATGTT ATATATAAAT      900

GATAAGAATA TACTGAAAAA TGTATCCAAA ATTTAAGGGG GCGTGTATAG TAAATAATTA      960

AAAGTATGTG CGTTGAAATA AATTTAGGAG GGTGGTTAGA TATGAATATA AATGACAACT     1020

TAAGTATAAA TTCCCCGGTA GATAATAAAA ATGTTGTAGT AGTTAGAGCT AGAAAAACTG     1080

ATACGGTTTT TAAGGCTTTT AAGGTTGCTC CCAATATTTG GGTGGCGCCA GAGAGATATT     1140

ATGGCGAATC TTTGAGTATA GATGAAGAAT ATAAAGTTGA TGGGGGAATA TATGATTCTA     1200

ATTTTCTTGG ATCCATGCCA TTTGTTAATA AACAATTTAA TTATAAAGAT CCTGTAAATG     1260

GTGTTGATAT TGCTTATATA AAAATTCCAA ATGCAGGACA AATGCAACCA GTAAAAGCTT     1320

TTAAAATTCA TAATAAAATA TGGGTTATTC CAGAAAGAGA TACATTTACA AATCCTGAAG     1380

AAGGAGATTT AAATCCACCA CCAGAAGCAA AACAAGTTCC AGTTTCATAT TATGATTCAA     1440

CATATTTAAG TACAGATAAT GAAAAAGATA ATTATTTAAA GGGAGTTACA AAATTATTTG     1500

AGAGAATTTA TTCAACTGAT CTTGGAAGAA TGTTGTTAAC ATCAATAGTA AGGGGAATAC     1560

CATTTTGGGG TGGAAGTACA ATAGATACAG AATTAAAAGT TATTGATACT AATTGTATTA     1620

ATGTGATACA ACCAGATGGT AGTTATAGAT CAGAAGAACT TAATCTAGTA ATAATAGGAC     1680

CCTCAGCTGA TATTATACAG TTTGAATGTA AAAGCTTTGG ACATGAAGTT TTGAATCTTA     1740

CGCGAAATGG TTATGGCTCT ACTCAATACA TTAGATTTAG CCCAGATTTT ACATTTGGTT     1800

TTGAGGAGTC ACTTGAAGTT GATACAAATC CTCTTTTAGG TGCAGGCAAA TTTGCTACAG     1860

ATCCAGCAGT AACATTAGCA CATGAACTTA TACATGCTGG ACATAGATTA TATGGAATAG     1920

CAATTAATCC AAATAGGGTT TTTAAAGTAA ATACTAATGC CTATTATGAA ATGAGTGGGT     1980

TAGAAGTAAG CTTTGAGGAA CTTAGAACAT TTGGGGGACA TGATGCAAAG TTTATAGATA     2040

GTTTACAGGA AAACGAATTT CGTCTATATT ATTATAATAA GTTTAAAGAT ATAGCAAGTA     2100

CACTTAATAA AGCTAAATCA ATAGTAGGTA CTACTGCTTC ATTACAGTAT ATGAAAAATG     2160

TTTTTAAAGA GAAATATCTC CTATCTGAAG ATACATCTGG AAAATTTTCG GTAGATAAAT     2220

TAAAATTTGA TAAGTTATAC AAAATGTTAA CAGAGATTTA CACAGAGGAT AATTTTGTTA     2280

AGTTTTTTAA AGTACTTAAC AGAAAAACAT ATTTGAATTT TGATAAAGCC GTATTTAAGA     2340

TAAATATAGT ACCTAAGGTA AATTACACAA TATATGATGG ATTTAATTTA AGAAATACAA     2400

ATTTAGCAGC AAACTTTAAT GGTCAAAATA CAGAAATTAA TAATATGAAT TTTACTAAAC     2460

TAAAAAATTT TACTGGATTG TTTGAATTTT ATAAGTTGCT ATGTGTAAGA GGGATAATAA     2520

CTTCTAAAAC TAAATCATTA GATAAAGGAT ACAATAAGTG ATAATCTAGA               2570
```